United States Patent [19]

Carson et al.

[11] Patent Number: 4,572,911

[45] Date of Patent: Feb. 25, 1986

[54] HEXAHYDROINDOLINZINE COMPOUNDS, PHARMACEUTICAL COMPOSITIONS AND METHODS AND INTERMEDIATES

[75] Inventors: John R. Carson, Norristown; Bruce E. Maryanoff, New Hope, both of Pa.

[73] Assignee: McNeilab, Inc., Fort Washington, Pa.

[21] Appl. No.: 636,885

[22] Filed: Aug. 2, 1984

[51] Int. Cl.$^4$ ............... C07D 491/147; C07D 471/14; C07D 471/04; C07D 31/44
[52] U.S. Cl. .................... 514/291; 514/292; 546/84; 546/89; 546/80; 546/114; 546/115; 546/121
[58] Field of Search ............ 546/84, 89, 80, 114, 546/115, 121; 424/256; 514/291, 292

[56] References Cited

U.S. PATENT DOCUMENTS 4,104,390 8/1978 Ferrand et al. ................ 424/256
4,315,938 2/1982 Schneider et al. ............. 424/267

FOREIGN PATENT DOCUMENTS 1299282 12/1972 United Kingdom .

OTHER PUBLICATIONS

Maryanoff; B. E., "Stereochemistry of Intramolecular Amidoalkylation Reactions in the Synthesis of Polycyclic Isoquinoline Derivatives", J. Org. Chem., vol. 48, No. 25, (12/16/83), pp. 5062-5074.

Journal of Medicinal Chemistry, vol. 8, (1965), pp. 265-267, S. Wawzonek and J. D. Nordstrom.
Heterocycles, vol. 22, No. 1, 1984, "Synthesis of the New Tricyclic System Thieno[3',2':3,4]Pyrido[1,2-a]-Pyrazine-4-One", Daniel Fréhel and Jean-Peirre Maffrand.
Australian Journal of Chemistry, vol. 37, No. 2, 1984, pp. 367-379, "Synthesis of 4H-Thieno[2,3-d]azonine and Thieno[2,3-d]azecine Derivatives".
Journal of Organic Chemistry, ". . . Synthesis of Heterocyclic Amines", Winn and Zaugg, vol. 33, No. 10, pp. 3779-3783, (1968).

Primary Examiner—Henry R. Jiles
Assistant Examiner—Dale A. Bjorkman
Attorney, Agent, or Firm—David J. Levy

[57] ABSTRACT

Hexahydroindolizines of the following formulae (I) and (II):

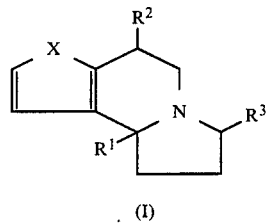

(I)

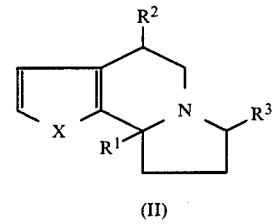

(II)

are novel and have been found to possess antisecretory and antidepressant properties. Methods of preparation, intermediates thereto and use are also disclosed.

17 Claims, No Drawings

HEXAHYDROINDOLINZINE COMPOUNDS, PHARMACEUTICAL COMPOSITIONS AND METHODS AND INTERMEDIATES

This invention relates to novel chemical compounds which are fused heteroaromatic derivatives of 4,5,7,8,9,9a-hexahydroindolizine found to be useful as gastric antisecretory agents and as antidepressants.

SUMMARY OF THE INVENTION

Hexahydroindolizines of the following formulae (I) and (II):

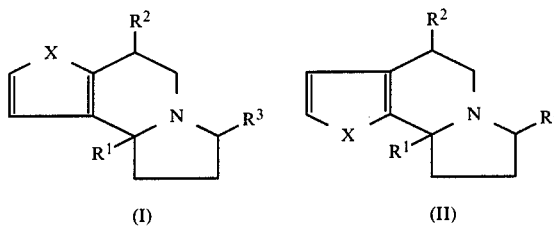

wherein X, $R^1$, $R^2$, and $R^3$ are as defined herein have been found to possess gastric antisecretory and antidepressant properties when administered to a mammal in need thereof. Intermediates thereto, pharmaceutical compositions containing compounds of formulae (I) and/or (II) and methods for treatment using such compositions are also part of the invention.

DETAILED DESCRIPTION OF THE INVENTION

Compounds of the invention are of the following formulae (I) and (II):

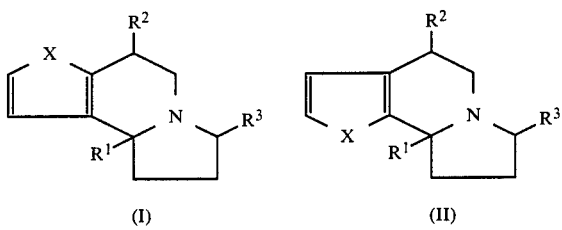

wherein
$R^1$ is hydrogen, alkyl, or phenyl;
$R^2$ is hydrogen, phenyl, a thiophene ring, a furan ring, a pyrrole ring, an N-alkylpyrrole ring or phenyl independently substituted with one or more of halogen and alkyl.
$R^3$ is hydrogen, phenyl or phenyl independently substituted with one or more of halogen, alkyl, alkoxy, or fluoroalkyl;
X is a sulfur or an oxygen atom or an $NR^4$ group; and,
$R^4$ is hydrogen, alkyl, phenyl, phenylalkyl, or phenylalkyl wherein the phenyl is independently substituted with one or more of halogen, alkyl, alkoxy, or fluoroalkyl, and the pharmaceutically acceptable acid addition salts thereof.

In particular, R is hydrogen; lower alkyl of about one to six carbon atoms; or phenyl.

$R^2$, in more detail, is hydrogen; phenyl; 2- or 3-thienyl; 2- or 3-furanyl; 2- or 3-pyrrolo; 2- or 3-pyrrolo substituted in the 1-position with lower alkyl of about one to six carbon atoms; or phenyl substituted by one, two or three substituents independently selected from halogen or lower alkyl of about one to six carbon atoms;

$R^3$ is, in more detail, hydrogen; phenyl; or phenyl substituted with one to three substituents independently selected from halogen, lower alkyl of about one to six carbon atoms, lower alkoxy of about one to six carbon atoms, or lower fluoroalkyl of about one to six carbon atoms.

X is a sulfur or an oxygen atom or an $NR^4$ group.

$R^4$, in more detail, is hydrogen; lower alkyl of about one to six carbon atoms; phenyl; phenyl lower alkyl of about one to six carbon atoms; or phenyl loweralkyl of about one to six carbon atoms, e.g., 1 to 3, in the alkyl portion wherein the phenyl is substituted with one, two or three substituents independently selected from halogen, loweralkyl of about one to six carbon atoms, lower alkoxy of about one to six carbon atoms, or lower fluoroalkyl of about one to six carbon atoms.

The pharmaceutically acceptable acid-addition salts of the compounds of formulae (I) and (II) include those of a mineral or organic acid such as hydrochloric, hydrobromic, hydroiodic, sulfuric, phosphoric, fumaric, maleic, cyclohexylsulfamic, citric, lactic, methanesulfonic, and similar acids.

As used herein, the terms "lower alkyl", "lower alkoxy" and "lower fluoro alkyl" to straight or branched-chain carbon skeletons within the carbon atom limits defined. For example, "lower alkyl" defines a methyl, ethyl, propyl, i-propyl, butyl, t-butyl and the like groups. "Lower alkoxy" defines methoxy, ethoxy, propoxy, i-propoxy, butoxy, t-butoxy and the like groups. "Phenyl lower alkyl" defines a benzyl, phenethyl, phenpropyl, and the like groups. "Lower fluoro alkyl" refers to lower alkyl groups substituted with at least one fluorine atom, such as trifluorormethyl, perfluoroethyl, 1,2-difluoroethyl, 1,1-difluoroethyl, 1,1,1-trifluoroethyl and the like groups. The term "halo" (or "halogen") includes fluorine, chlorine, bromine, and iodine.

Each formula (I) or formula (II) compound describes and comprises diastereomeric substances, themselves pairs of enantiomers. The diastereomers, isolated in their pure form, may differ in biological activity. The novel compounds of formulae (I) and (II) constitute valuable therapeutic agents by their possession of gastric acid secretion inhibition and antidepressant activity. The various diastereomers of each formula (I) or formula (II) compound are distinguished herein using the nomenclature system recommended by Chemical Abstracts for representing the relative configurations of diastereomers of fused-ring compounds, i.e., alpha or beta nomenclature. This requires that the stereocenter corresponding to the lowest numbered atom in the ring system (numbered according to convention) be designated "alpha" and that the remaining stereoceter be designated "alpha" or "beta" relative to the first-assigned center. For example:

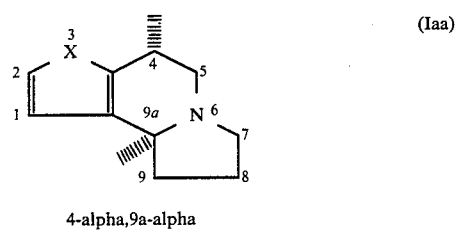

4-alpha,9a-alpha

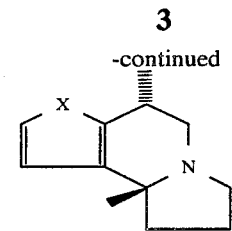

4-alpha,9a-beta

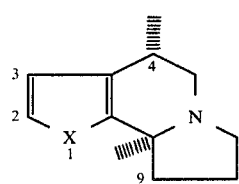

4-alpha,9a-alpha

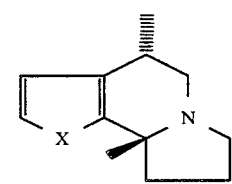

4-alpha,9a-beta

The compounds of formulae (I) and (II) may be prepared by the following Routes (A), (B), (C) and (D).

(A) Keto-Acid, Lactam Route:

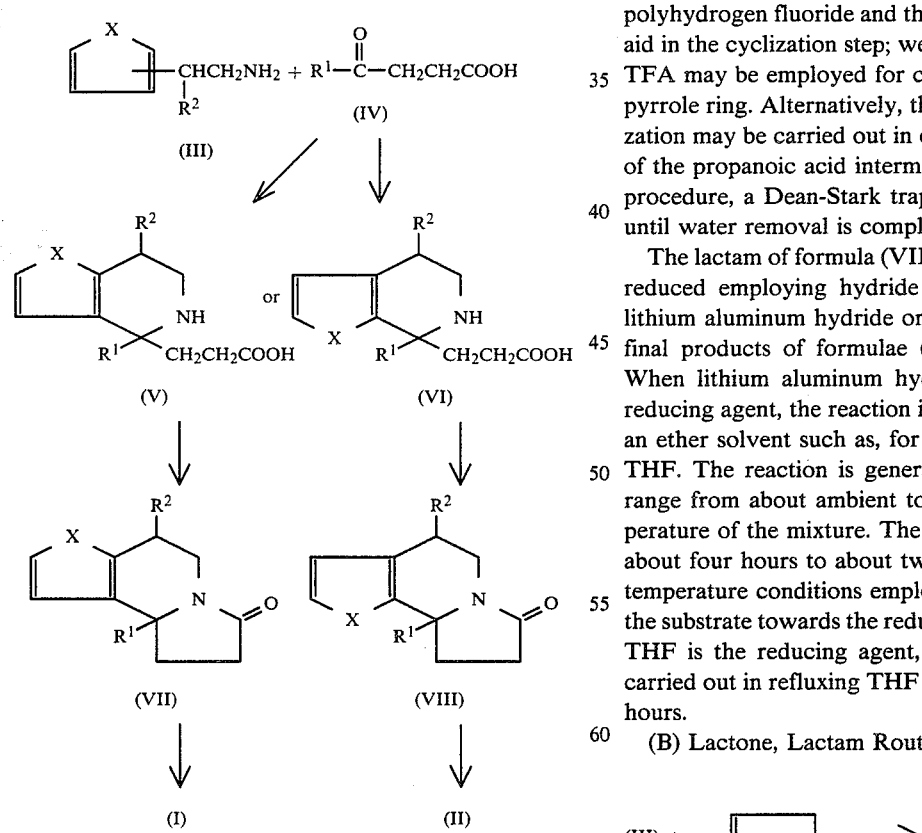

Compounds of formula (I) or (II) wherein $R^3$ is hydrogen may be prepared by the (A) route shown above. In the first step, a substituted heterocyclic ethyl amine of formula (III) is reacted with a keto acid of formula (IV) to form an intermediate propanoic acid of formula (V) or (VI). The propanoic acid of formula (V) or VI) is then cyclized to construct a lactam of formulae (VII) or (VIII), respectively. The position of the aminoethyl side-chain on the compounds of formula (III) determines whether the acid formed is of formula (V) or (VI). Thus, when the aminoethyl side-chain is on the 2-position of the heterocyclic ring, the resulting acid is of formula (V); and, when the aminoethyl side-chain is on the 3-position of the heterocyclic ring, the resulting lactam is of formula (VI). The lactams of formula (VII) or (VIII) are subsequently reduced to form the compounds of the invention of formula (I) or (II) wherein $R^3$ is hydrogen.

More specifically, a heterocyclic 2- or 3-ethylamine of formula (III) is condensed with levulinic acid (or congeners thereof of formula (IV) in a refluxing solvent such as benzene or toluene for a period of about 2 to 5 hours to form a propanoic acid intermediate of formula (V) or (VI), respectively. The propanoic acid intermediate of formula (V) or (VI) is then cyclized to the lactam of formula (VII) or (VIII), respectively, by refluxing in an inert, high-boiling solvent such as benzene, toluene, xylene or methylcellosolve under a Dean-Stark trap until removal of water is complete. A catalytic amount of a strong acid such as para toluenesulfonic, polyphosphoric, liquid hydrogen fluoride, pyridinium polyhydrogen fluoride and the like may be employed to aid in the cyclization step; weaker acids such as HCl or TFA may be employed for cyclization onto a furan or pyrrole ring. Alternatively, the condensation and cyclization may be carried out in one step, without isolation of the propanoic acid intermediate (V) or (VI). In this procedure, a Dean-Stark trap is employed throughout until water removal is complete.

The lactam of formula (VII) or (VIII) is subsequently reduced employing hydride reducing agents such as lithium aluminum hydride or borane-THF to yield the final products of formulae (I) and (II), respectively. When lithium aluminum hydride is employed as the reducing agent, the reaction is preferably carried-out in an ether solvent such as, for example, diethyl ether or THF. The reaction is generally run at a temperature range from about ambient to about the refluxing temperature of the mixture. The reaction time varies from about four hours to about two days, depending on the temperature conditions employed and the reactivity of the substrate towards the reducing agent. When borane-THF is the reducing agent, the reaction is generally carried out in refluxing THF for a period of about 1.5-2 hours.

(B) Lactone, Lactam Route:

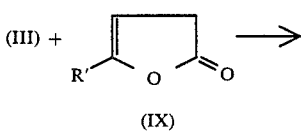

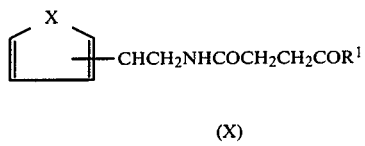

(X)

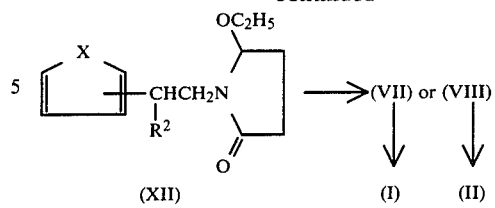

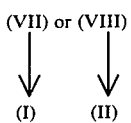

(I)   (II)

Compounds of formula (I) or (II) wherein $R^3$ is hydrogen may also be prepared by the (B) route shown above. In the first step, a substituted heterocyclic ethylamine of forumula (III) is reacted with an alpha-angelicalactone (or congeners thereof) of formula (IX) to form an intermediate amido ketone of formula (X). The position of the aminoethyl side-chain on the compounds of formula (III) determines the position of the amidoketone side-chain on the compounds of formula (X) and subsequently the lactam structure (VII) or (VIII). Thus, when the aminoethyl side-chain is on the 2-position of the heterocyclic ring, the resulting lactam is of formula (VII); and, when the aminoethyl side-chain is on the 3-position of the heterocyclic ring, the resulting lactam is of formula (VIII). The lactams of forumla (VII) or formula (VIII) are subsequently reduced as described in Route (A) to form the compounds of the invention of formula (I) or (II) wherein $R^3$ is hydrogen.

More specifically, a heterocyclic ethylamine of formula (III) is condensed with the alpha-angelicalactone in a refluxing solvent such as toluene, THF or methylene chloride for about one to six hours to form a keto-amide of formula (X). The keto-amide is then cyclized by heating in a solvent such as absolute ethanol or toluene in the presence of a strong acid such as hydrogen chloride, methane sulfonic or trifluoroacetic acid for a period of about two to eight hours to yield a lactam of formula (VII) or (VIII). In the last step of this method, the lactam is reduced as described for Route (A) to yield the final products of formulae (I) and (II), respectively, wherein $R^3$ is hydrogen.

(C) Imide, Acyliminium-Ion Route:

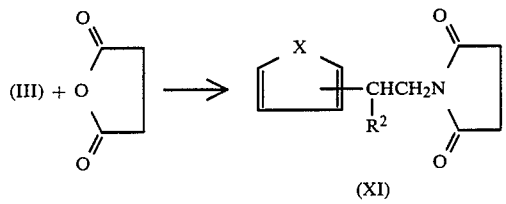

The imide, acyliminium route (C) yields compounds of formula (I) or formula (II) wherein R is hydrogen. An ethylamine of formula (III) is first reacted in two steps with succinic anhydride (or congeners thereof) to form an imide of formula (XI). The imide is then reduced with sodium borohydride in ethanol in the presence of excess methanesulfonic acid as described by Speckamp, et al. in Tetrahedron, Vol. 31, page 1437 (1975) to form an ethoxy species of formula (XII). Cyclization of (XII) in the presence of a strong acid yields a lactam of formula (VII) or (VIII). In the case of furan and pyrrole compounds of formula (XI), cyclization may take place simultaneously under the conditions described for the sodium borohydride reduction.

More particularly, a heterocyclic ethylamine of formula (III) is treated with a solution of succinic anhydride in an inert solvent such as THF or methylene chloride followed by removal of the solvent and heating of the resulting residue (an amide-acid intermediate; structure not shown) at a temperature of about 130° C. to about 180° C. to yield an imide of formula (XI). The imide is next treated with ethanol and sodium borohydride at a temperature of about $-5°$ C. to 5° C. followed by dropwise addition of excess 2N methane sulfonic acid in ethanol over a period of about three to six hours so that the final pH is about 1 to 3. The temperature is allowed to warm to ambient while stirring for an additional eight to twenty-four hours to yield an ethoxy intermediate of formula (XII). The ethoxy intermediate is cyclized by reacting at a temperature of about 25° C. to 110° C. in an inert solvent such as ethanol or toluene in the presence of an anhydrous strong acid such as hydrogen chloride, methane sulfonic or trifluoroacetic acid for a period of about two to five hours to yield a lactam of formula (VII) or (VIII). The lactam is then reduced as described for Route (A) to yield the final products of formula (I) or (II), respectively, wherein $R^1$ is hydrogen.

(D) Alkylation Route:

Compounds of formulae (I) or (II) wherein $R^3$ is other than hydrogen, particularly wherein $R^3$ is phenyl or substituted phenyl, are prepared by reaction of a lactam of formula (VII) or (VIII) with phenyl lithium or a substituted phenyl lithium derivative to form an intermediate substituted tetrahydroindolizine of formulae (XIII) or (XIV), followed by reduction. In the case where a substituted phenyllithium is used, the substituted phenyllithium may be prepared by transmetallation of an appropriately substituted phenyl compound with butyllithium by methods well-known in organic chemistry.

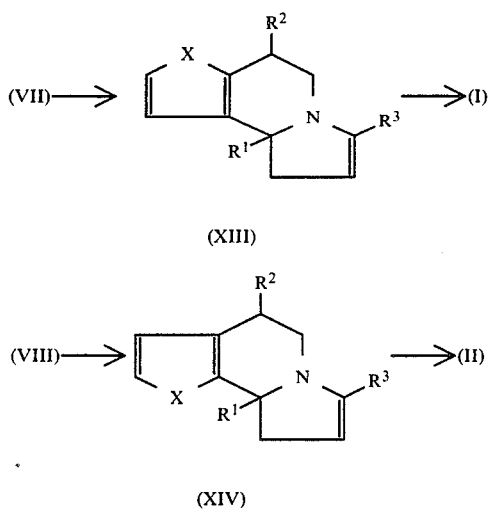

In particular, a compound of formulae (VII) or (VIII) in an inert anhydrous solvent such as anhydrous THF or diethyl ether is treated with a solution of phenyllithium or a substituted phenyllithium in an inert solvent such as ether at a temperature of about 5° C. to about the reflux temperature of the solvent to form an intermediate tetrahydroindolizine of formulae (XIII) or (XIV). The alkene is subsequently reduced by the action of a solution of LiAlH$_2$Cl$_2$ (freshly prepared from equimolar amounts of LAH and anhydrous aluminum chloride) in a dry inert solvent such as anhydrous diethyl ether. The reaction mixture is stirred for a period of about 1 to 150 hours at a temperature of about 0° to 50° C. to yield the products of formulae (I) and (II) in their free base form.

The cyclization reactions in routes (A)-(C) afford mixture of diastereomers. In certain instances, product mixture may be highly enriched in specific diastereomers. The diastereomers may be separated and purified by standard techniques known to those skilled in the art of organic chemistry, such as fractional crystallization or liquid chromatography of free bases, or fractional crystallization of acid-addition salts.

Diastereomers may be interconverted by treatment with a base. Specifically, heating of lactam diastereomers of formulae (VII) or (VIII) wherein R$^1$ and/or R$^2$ are hydrogen atoms in aqueous DMSO at a temperature of about 100° to 150° C. in the presence of an alkali metal carbonate, such as K$_2$CO$_3$, for a period of about 40 minutes to three days gives rise to equilibrium mixtures of diastereomers. Similarly, heating of the amine diastereomers of formulae (I) or (II) wherein R$^1$ and/or R$^2$ are hydrogen atoms in aqueous DMSO at about 80° to 150° C. in the presence of an alkali metal hydroxide such as NaOH for a period of about 1 to 120 hours, can give rise to equilibrium mixtures of diastereomers. Such equilibration methods can enhance the proportions of minor diastereomers in comparison to the original product mixtures from cyclization. In appropriate instances, the equilibration method can alter relative configuration between the stereocenters involved.

Because the subject compounds of formula (I) and (II) possess a basic nitrogen atom, they may be converted into the corresponding acid addition salts.

The acid addition salts may be prepared by reaction with an appropriate acid, as for example, an inorganic acid such as a hydrohalic acid, i.e., hydrochloric, hydrobromic or hydroiodic acid; sulfuric or nitric acid; phosphoric acid; an organic acid such as acetic, propionic, glycolic, pamoic, pyruvic, malonic, succinic, maleic, picric, fumaric, malic, tartaric, citric, benzoic, cinnamic, mandelic, methanesulfonic, ethanesulfonic, benzenesulfonic, p-toluenesulfonic, salicylic, 2-naphthalenesulfonic or p-aminosalicylic acid. The therapeutically active, nontoxic acid addition salts of subject compounds of formula (I) and (II) are included within the scope of the present invention.

In addition to the novel compounds of formulae (I) and (II), novel intermediates of formulae (V), (VI), (VII), (VIII), (XIII) and (XIV) are included in this invention as being useful as intermediates in the preparation of the active compounds of formulae (I) and (II). When these intermediates possess a basic center and/or an acidic center, the acid addition salts and base addition salts thereof are also included within the scope of the invention.

Acute Gastric Fistula Rat Test

The compounds of the invention are useful for inhibition of gastric acid secretion as measured by the following test. Female Sprague-Dawley rats are fasted twenty-four hours before testing and are given water ad libidum while being kept in individual cages. On the day of testing, the rats are weighed and are selected so that the rats in each test weigh within a range of ±20 grams.

Surgery is carried out under light ether anesthesia. As soon as the rat is anesthetized its teeth are removed and a mid-line incision is made on the abdomen about 1½ inches in length and the stomach and duodenum are exposed. If at this point the stomach is filled with food or fecal material, the rat is not used. If the condition of the stomach is acceptable, a purse string stitch is placed on the fundic portion of the stomach with a suture, taking care not to pierce any blood vessels in the area. A small nick is then made into the stomach in the center of the purse string, and a cannula, consisting of a small vinyl tube with a flange on one end, is put into the stomach, and the purse string stitch is closed tightly around the flange. The test compound is administered intraduodonally (i.d.) immediately after surgery in a volume of 0.5 ml/100 grams rat. Control rats receive the test vehicle, 0.5% aqueous methyl cellulose.

After the surgery and after administration of the test compound, the abdominal wall and skin are closed simultaneously with three or four 10 mm wound clips and a collecting tube is placed on the cannula. Each rat is then placed in a box in which a longitudinal slit has been made to allow the cannula to hang freely and to allow the rat to move about unencumbered. After the rat has been allowed to stabilize for thirty minutes, the collection tube on the cannula is discarded and replaced with a clean tube to receive the gastric juice. Collections are made at one hour.

The sample of gastric contents collected is drained into a centrifuge tube and centrifuged to pack down the sediment. The volume is read and a 1 ml aliquot of the supernatant is put into a beaker containing 10 ml distilled water and is titrated to pH 7 using 0.01 N sodium hydroxide. Results are determined for Volume, Titratable Acid and Total Acid Output, where Volume equals total ml of gastric juice minus sediment; Titratable Acid (meq/1) equals amount of 0.01 N sodium hydroxide needed to titrate the acid to pH 7; and Total Acid Output equals Titratable Acid times Volume. Results are reported as % inhibition of Total Acid Output (TAO) for a dose of 20 mg/kg i.d. of the compound of formula (I) or (II). Particularly useful are compounds having significant inhibition of TAO at a dose of 20 mg/kg.

It is well-known that excessive secretion of gastric hydrochloric acid leads to unneeded peptic activity and endangers the mucous lining of the duodenum. The use of gastric antisecretory agents is thus desirable as an aid in the prevention and amelioration of distress occasioned by high concentration of stomach acid.

The pharmacological effect of the compounds of the present invention as inhibitors of gastric acid secretion, is shown in Table I below.

TABLE I

| Acute Gastric Fistula Rat Screen | |
|---|---|
| Compound of Example No. | % Inhibition of TAO @ 20 mg/kg i.d. |
| 4 | 78 |
| 5 | 66 |
| 7 | 86 |
| 10 | 82 |
| 12 | 37 |
| 13 | 74 |
| 16 | 86 |
| 17 (1st) | 90 |
| 17 (2nd) | 88 |
| 18 | 100 |
| 19 (1st) | 98 |
| 19 (2nd) | 98 |
| 19 (3rd) | 88 |
| 20 (1st) | 47 |
| 20 (2nd) | 41 |

In addition to their utility in the treatment of excessive gastric acid secretion, compounds of formulae (I) and (II) exhibit useful biological activity in the central nervous system. More particularly, they exhibit antidepressant activity in warm-blooded animals.

The central nervous system utility of the novel compounds of this invention is based on a standard test for antidepressant agents involving antagonism of the depressant effects of tetrabenazine (TBZ). This is the "classical" tetrabenazine antagonism assay described in U.S. Pat. No. 3,787,577. Mice are injected with a test compound 30 minutes prior to the injection of 32 mg/kg i.p. of TBZ, a drug which decreases normal exploratory activity and induces ptosis. After 30 minutes, the mice are tested for two parameters: the presence of normal exploratory activity (EA) and reversal of ptosis (Pt). A control group of mice is given only 32 mg/kg i.p. of TBZ. The biological activity of the novel compounds of this invention compared to imipramine may be understood by some representative, nonlimiting examples, presented in TABLE II.

TABLE II

| TETRABENZINE ANTAGONISM ASSAY | |
|---|---|
| Compound of Ex. No. | TBZ ED$_{50}$ EA/Pt mg/kg (i.p.) |
| 17 (2nd) | 2.4/Ca. 0.75 |
| 20 (2nd) | Ca. 24/Ca. 30 |
| Imipramine | 1.2/0.5 |

Methods of Treatment and Pharmaceutical Compositions

In view of the antisecretory activity of the subject compounds of formulae (I) and (II), there is further provided herein a method of inhibiting gastric acid secretion which comprises internally administering to a gastric hyperacidic subject (man or animal) an effective gastric acid secretion inhibiting amount of a compound of formula (I) or (II), in base or acid addition salt form, preferably in admixture with a pharmaceutically acceptable carrier. Pharmaceutical compositions comprising a subject compound (I) or (II) are also considered a further aspect of the present invention.

Additionally, in view of the antidepressant activity of the subject compounds of formula (I) and (II), there is further provided herein a method of treating depression which comprises internally administering to a depressed subject (particularly a human subject) an effective antidepressant amount of a compound of formula (I) or (II) in base or acid addition salt form, preferably in admixture with a pharmaceutically-acceptable, non-toxic carrier.

For the treatment of excess gastric acid secretion or depression, compounds of the present invention of the formula (I) or (II) may be administered orally or parenterally in a pharmaceutical composition comprising about 10 to 4000 mg, preferably about 20 to 2000 mg of one or more of the subject compounds per day for an average adult human depending on the activity of the particular compound chosen. The dosage may be divided into 1 to 4 unit dosage forms per day. While the therapeutic methods of the invention are most useful for human subjects in need of alleviation of excess gastric acid secretion or depression, the compounds may be administered to other mammals at comparable dosages per weight of the subject.

To prepare the pharmaceutical compositions of this invention, one or more compounds or salt thereof of the invention as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

More particularly, a pharmaceutical composition useful for inhibiting gastric acid secretion will contain per unit dosage from about 5 to about 1000 mg of the active ingredient, and, preferably, from about 10 to about 400 mg. A pharmaceutical composition useful for treating depression will contain per unit dosage from about 5 to about 500 mg of the active ingredient, and, preferably, from about 5 to about 250 mg. The total daily dosage may be divided into 1 to 4 unit dosage forms per day.

The following examples are intended to illustrate but not to limit the scope of the present invention.

In the following Examples and throughout the specification, the following abbreviations may be used: mg (milligrams); g (grams); kg (kilograms); mm (millimeters); l (liters); mmole (millimoles); M (molar); N (normal); psi (pounds per square inch); mp (melting point); bp (boiling point); dec (decomposes); meq (milliequivalents); E (trans); Z (cis); Et₂O (diethyl ether); EtOAc (ethyl acetate); MeOH (methanol); EtOH (ethanol); i-PrOH (isopropanol); LAH (lithium aluminum hydride); TFA (trifluoroacetic acid); DMSO (dimethylsulfoxide); THF (tetrahydrofuran); DMF (dimethylformamide); i.p. (intraperitoneal); TAO (total acid output); HPLC (high pressure liquid chromatography); and C,H,N,O, etc. (the chemical symbols for the elements). Unless otherwise indicated, all temperatures are reported in °C. (degrees centigrade).

EXAMPLE 1

4,5,6,7-Tetrahydro-4-methyl-1H-pyrrolo[3,2-c]pyridine-4-propanopic acid propanoic acid Formula (V):

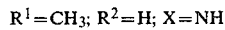

R¹=CH₃; R²=H; X=NH

To a solution of 81.6 g (0.704 mole) of levulinic acid in 1.5 liters of benzene was added 70.4 g (0.64 mole) of 2-(2-aminoethyl)pyrrole in 1 liter of benzene. The solution was heated at reflux for 4½ hours with the azeotropic removal of water. The mixture was cooled, and the precipitate collected and air dried to give 106 g of a gray solid which was crystallized from ethanol/water to give the title compound, a white solid, mp 206°–210° (dec).

EXAMPLE 2

4,5,7,8,9,9a-Hexahydro-9a-methyl-3H-pyrrolo[2,3-g]indolizin-7-one

Formula (VII)

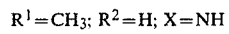

R¹=CH₃; R²=H; X=NH

A solution of 95.4 (0.46 mole) of 4,5,6,7-tetrahydro-4-methyl-1H-pyrrolo[3,2-c]pyridine-4-propanoic acid, the product of Example 1, in 2 liters of methyl cellosolve was heated at reflux for four hours. The solvent was evaporated at reduced pressure, and the residue washed twice with benzene. The benzene extracts were washed successively with 1N hydrochloric acid, aqueous sodium bicarbonate, and brine, then dried over anhydrous magnesium sulfate and evaporated at reduced pressure to give 9.8 g (11%) of the title compound, a tan solid, mp 185°–188° C.

EXAMPLE 3

3-(2-Chlorobenzyl)-4,5,7,8,9,9a-hexahydro-9a-methyl-3H-pyrrolo[2,3-g]indolizin-7-one Formula (VII):

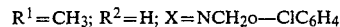

R¹=CH₃; R²=H; X=NCH₂o—ClC₆H₄

To a suspension of 5.5 ml of 35% potassium hydride in oil under nitrogen was added 70 ml of dry dimethylsulfoxide. A solution of 7.1 g of 4,5,7,8,9,9a-hexahydro-9a-methyl-3H-pyrrolo[2,3-g]indolizin-7-one, the product of Example 2, in 60 ml of dry dimethylsulfoxide was added with cooling. The resulting mixture was stirred at room temperature for 1½ hours. A solution of 5.96 g (0.037 mole) of alpha,2-dichlorotoluene in 30 ml of dry dimethylsulfoxide was added and stirring continued for three hours. The mixture was then heated at 55° C. for one hour and allowed to stir at room temperature overnight. The reaction mixture was extracted three times with hexane, then poured into 550 ml of water. The aqueous layer was extracted with methylene chloride. The combined extracts were washed with brine, dried over anhydrous magnesium sulfate, and evaporated to give 10.5 g (90%) of title compound, a dark oil.

EXAMPLE 4

3-(2-Chlorobenzyl)-4,5,7,8,9,9a-hexahydro-9a-methyl-3H-pyrrolo[2,3-g]indolizine

Formula (I):

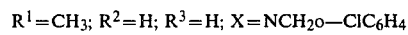

R¹=CH₃; R²=H; R³=H; X=NCH₂o—ClC₆H₄

A solution of 12.5 g of 3-(2-chlorobenzyl)-4,5,7,8,9,9a-hexahydro-9a-methyl-3H-pyrrolo[2,3-g]indolizin-7-one, the product of Example 3, in 300 ml of ether was added under nitrogen to a slurry of 3.8 g (0.1 mole) of LAH in 50 ml of ether. This mixture was stirred at room temperature overnight then heated at reflux for five hours. Excess hydride was destroyed with 3.8 ml of water, 3.8 ml of 10% aqueous sodium hydroxide, and 10 ml of water. The white precipitate was removed by filtration and washed well with ether. The filtrate was evaporated in vacuo to obtain a yellow oil which was distilled at 140° C. and 0.025 Torr to give 6.42 g of an oil. This oil was taken up in an equal volume of methylcyclohexane and crystallized to give 3.4 g (28%) of the title compound, a tan solid, mp 58°–61° C.

Elemental Analysis: Calculated for C₁₈H₂₁ClN₂: C, 71.87; H, 7.04. Found: C, 71.65; H, 7.10.

EXAMPLE 5

4,5,7,8,9,9a-Hexahydro-9a-methyl-3H-pyrrolo[2,3-g]indolizine E-(2-)butenedioate(1:1)

Formula (I):

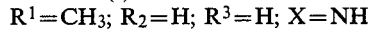

R¹=CH₃; R2=H; R³=H; X=NH

A slurry of 3.04 g (0.08 mole) of LAH in 40 ml of dry THF under argon was treated with a solution of 6.17 g (0.032 mole) of 4,5,7,8,9,9a-hexahydro-9a-methyl-3H-pyrrolo[2,3-g]indolizin-7-one, the product of Example 2, in 120 ml of THF over a period of 15 minutes. The mixture was stirred overnight at room temperature, then heated at reflux for four hours. The excess hydride was decomposed with 3 ml of water, 3 ml of 10% sodium hydroxide, and 7 ml of water. The resulting white precipitate was filtered off and washed several times with THF. The combined filtrate and washings were evaporated at reduced pressure to give 5.1 g of an oil. This material was taken up in hot i-PrOH and added to a solution of 2.09 g of fumaric acid in hot i-PrOH. The fumarate salt was recrystallized from i-PrOH to give 2.85 g (31% yield) of title compound, mp 173°–175° (dec).

Elemental Analysis: Calculated for C₁₅H₂₀N₂O₄: C, 61.24; H, 6.97. Found: C, 61.24; N, 6.96.

Sample contains 4% i-PrOH and 10% water.

EXAMPLE 6

4,5,6,7,8,9,9a-Hexahydro-3-methyl-9a-phenyl-3H-pyrrolo[2,3-g]indolizin-7-one Formula (VII):

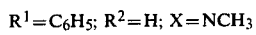

$R^1=C_6H_5$; $R^2=H$; $X=NCH_3$

A suspension of 16 g (0.129 mole) of 2-(2-aminoethyl)-1-methylpyrrole and 25.3 g (0.142 mole) of 3-benzoylpropionic acid in 600 ml of xylene was refluxed with a Dean-Stark trap until 4.2 ml of water had been collected. The xylene was evaporated in vacuo, the residue dissolved in methylene chloride and washed successively with dilute hydrochloric acid, 5% sodium bicarbonate solution, and brine. The methylene chloride layer was dried over anhydrous magnesium sulfate and evaporated in vacuo to give 29.9 g of residue which was chromatographed on silica gel and eluted with petroleum ether. Fractions enriched with product were combined, and evaporated in vacuo to give a brownish yellow oil which crystallized from cyclohexane to give 6.3 g of a yellow solid, mp 130°-133° C. This material was recrystallized from methanol to give 2.7 g of title compound, mp 133°-135° C.

EXAMPLE 7

4,5,7,8,9,9a-Hexahydro-3-methyl-9a-phenyl-3H-pyrrolo[2,3-g]indolizine

Formula (I):

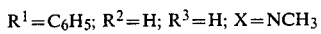

$R^1=C_6H_5$; $R^2=H$; $R^3=H$; $X=NCH_3$

A solution of 5.95 g (0.0224 mole) of 4,5,7,8,9,9a-hexahydro-3-methyl-9a-phenyl-3H-pyrrolo[2,3-g]indolizin-7-one, the compound of Example 6, in 400 ml of ether was added to a suspension of 1.71 g (0.0448 mole) of LAH in 35 ml of ether under argon. The mixture was stirred at ambient temperature overnight. After the addition of water and 10% sodium hydroxide solution, the resulting white precipitate was filtered off and the filtrate evaporated in vacuo to give 5.5 g of a light green oil. The oil was crystallized from methanol to give 3.3 g (61%) of the title compound, a white solid, mp 71°-73° C.

Elemental Analysis: Calculated for $C_{17}H_{20}N_2$: C, 80.91; H, 7.99; N, 11.10. Found: C, 81.09; N, 7.67; N, 11.05.

EXAMPLE 8

2-(1-Phenylpyrrol-2-yl)ethylamine E-(2)-butenedioate (2:1)

Formula (III):

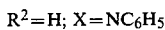

$R^2=H$; $X=NC_6H_5$

A mixture of 175 g (0.87 mole) of 2,5-dimethoxytetrahydro-2-furaldedimethylacetal and 81 g (0.87 mole) of aniline in 400 ml of glacial acetic acid was heated at reflux for 30 minutes, then the solvent was evaporated at reduced pressure. The residue was taken up in 240 ml of dioxane, 87 ml of 0.5N hydrochloric acid added, and the mixture heated at reflux for five minutes, cooled, poured into one liter of water and extracted five times with ether. The combined ether extracts were washed with water, sodium bicarbonate solution, and brine, then dried over anhydrous magnesium sulfate. The water wash was extracted three times with ether. The combined ether extracts were washed and dried as above. The two ether solutions were combined and evaporated at reduced pressure to give 160 g of a dark oil. The oil was taken up in ether, and chromatographed on neutral alumina, eluting with ether. A dark oil was obtained (134.3 g), which was crude N-phenylpyrrole-2-carboxaldehyde.

A solution of 134.3 g (0.785 mole) of the crude aldehyde in 225 ml of absolute ethanol, 13.6 ml of N-benzylamine, 10 ml of glacial acetic acid, and 54 ml (0.785 mole) nitromethane was stirred at about 40° C. for 1.5 hrs. On cooling, a dark precipitate formed and was collected by filtration to give 111.4 g of dark brown solid. An ethereal solution of this solid was filtered through dicalite and evaporated at reduced pressure to give 110.6 g (66%) of a dark solid, mp 86°-89° C., which was 1-nitro-2-(1-phenylpyrrol-2-yl)ethene.

A slurry of 79 g (2.08 moles) of LAH in 800 ml of THF was treated slowly with a solution of 110.6 g (0.52 mole) of the nitro compound in 450 ml of THF. This mixture was heated at reflux for eight hours and stirred at room temperature for 36 hours. Excess hydride was decomposed by very careful addition of 79 ml of water, 79 ml of 10% sodium hydroxide and 79 ml of water. The resulting light tan precipitate was collected by filtration and washed well with THF. The filtrate was evaporated at reduced pressure to afford 89.5 g of dark brown oil. The oil was distilled at 94°-97° C./0.1 Torr to give 57 g of free base, a colorless oil. A solution of 7.0 g (0.038 mole) of this oil in 20 ml of hot i-PrOH was treated with a solution of 2.18 g (0.019 mole) of fumaric acid in 50 ml of hot i-PrOH. On cooling, the white precipitate was collected by filtration and recrystallized from absolute ethanol to give the title compound, mp 169°-170.5° C.

EXAMPLE 9

4,5,7,8,9,9a-Hexahydro-9a-methyl-3-phenyl-3H-pyrrolo[2,3-g]indolizin-7-one

Formula (VIII):

$R^1=CH_3$; $R^2=H$; $X=NC_6H_5$

A solution of 34.4 g (0.296 mole) of levulinic acid in 625 ml of toluene was added to a solution of 50 g (0.269 mole) of 2-(1-phenylpyrrol-2-yl)ethylamine, the free base of Example 8. The mixture was heated at reflux for four hours and 9.4 ml of water was collected in a Dean-Stark trap. When the heat source was removed, the clear orange solution turned red. Another 800 ml of toluene were added and the solution was washed twice with 1N hydrochloric acid, twice with aqueous sodium bicarbonate, once with water, then brine, dried over anhydrous magnesium sulfate and evaporated at reduced pressure to obtain 74.3 g of a brown oil. The oil was crystallized from 350 ml of i-PrOH to obtain 41.9 g of a tan solid. Concentration of the mother liquor gave another 4.9 g. One recrystallization from i-PrOH gave pure title compound, mp 145°-147.5° C.

EXAMPLE 10

4,5,7,8,9,9a-Hexahydro-9a-methyl-3-phenyl-3H-pyrrolo[2,3-g]indolizine

Formula (I):

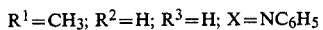

$R^1=CH_3$; $R^2=H$; $R^3=H$; $X=NC_6H_5$

To a suspension of 5.2 g (0.14 mole) of LAH in 450 ml of ether under nitrogen was added 14.7 g (0.055 mole) of 4,5,7,8,9,9a-hexahydro-9a-methyl-3-phenyl-3H-pyrrolo-[2,3-g]indolizin-7-one, the compound of Example 9. The mixture was stirred at ambient temperature for two days. Excess hydride was decomposed by careful addition of 5.2 ml of water, 5.2 ml of 10% sodium hydroxide and 5.2 ml of water. The white precipitate was collected by filtration and washed well with ether. The filtrate was evaporated in vacuo to obtain 14.5 g of a white solid. Recrystallization from 200 ml of hexane afforded 12.1 g (87%) of the title compound, mp 111°–113° C.

Elemental Analysis: Calculated for $C_{17}H_{20}N_2$: C, 80.91; H, 7.99. Found: C, 80.78; H, 7.91.

EXAMPLE 11

3,9a-Dimethyl-4,5,7,8,9,9a-hexahydro-3H-pyrrolo-[2,3-g]indolizin-7-one

Formula (VII):

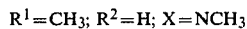

$R^1=CH_3; R^2=H; X=NCH_3$

A stirred solution of 76.5 g (0.66 mole) of levulinic acid in 1.1 liters of benzene was treated with a solution of 74.8 g (0.6 mole) of 2-(2-aminoethyl)-1-methylpyrrole in 550 ml of benzene and refluxed for 4.5 hours. A solution of 0.5 g of p-toluenesulfonic acid in 40 ml of benzene was added and the mixture refluxed for two more hours with azeotropic removal of water. The reaction was cooled, 250 ml of 1N hydrochloric acid added and the organic layer was washed two more times with 1N hydrochloric acid. The benzene solution was washed with sodium bicarbonate solution, brine, dried over anhydrous magnesium sulfate and evaporated in vacuo to yield 95.5 g of a brown solid. Recrystallization from cyclohexane gave 85 g (69%) of the title compound, a tan solid, mp 103°–106° C.

EXAMPLE 12

7-(4-Chlorophenyl)-4,5,7,8,9,9a-hexahydro-3,9a-dimethyl-3H-pyrrolo[2,3-g]indolizine (E)-2-butenedioate (1:7) hydrate (1:2)

Formula (I):

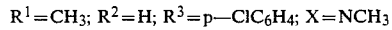

$R^1=CH_3; R^2=H; R^3=p-ClC_6H_4; X=NCH_3$

To a stirred solution of 36.3 g (0.19 mole) of 4-bromochlorobenzene in 100 ml of dry ether under nitrogen was added with cooling 137 ml of a 0.39M hexane solution of n-butyllithium. Stirring was continued at room temperature for two hours. This mixture was added under nitrogen to a vigorously stirred suspension of 35 g (0.17 mole) of 3,9a-dimethyl-4,5,7,8,9,9a-hexahydro-3H-pyrrolo[2,3-g]indolizin-7-one, the compound from Example 11, in 800 ml of dry ether in a Morton flask. The resulting brown suspension was stirred overnight at room temperature. The reaction mixture was poured into 300 ml of 1N phosphoric acid and 400 ml of ice water, stirred for ten minutes, then basified with 50% aqueous sodium hydroxide. The aqueous layer was separated and extracted twice with methylene chloride. The combined organic extracts were washed with water, then brine, dried over anhydrous sodium sulfate and evaporated at reduced pressure to obtain a dark viscous residue. Crystallization from methanol gave 20.3 g (40%) of an orange-brown solid which was 7-(4-chlorophenyl)-4,5,9,9a-tetrahydro-3,9a-dimethyl-3H-pyrrolo[2,3-g]indolizine, mp 143°–148° dec.

A solution of 6.27 g (0.047 mole) of aluminum trichloride in 100 ml of dry ether was added in one portion to 36.2 ml of 1.3M ethereal solution of LAH and stirred at room temperature for 45 minutes. To the resulting mixture was added 28.9 g of 7-(4-chlorophenyl)-4,5,9,9a-tetrahydro-3,9a-dimethyl-3H-pyrrolo[2,3-g]indolizine as prepared above over a period of ten minutes. The tan suspension was stirred for six days.

Excess hydride was destroyed by addition of 15 ml of 10% aqueous sodium hydroxide, and the reaction mixture poured into 150 ml of 1N sodium hydroxide followed by filtration through filter aid. The aqueous layer was separated and extracted with ether. The combined ether extracts were washed twice with water, once with brine, dried over anhydrous potassium carbonate and evaporated at reduced pressure to yield 11.2 g of brown residue, an oil. A solution of 3.5 g of fumaric acid in hot i-PrOH was added to a solution of 9.2 g of the oil in i-PrOH. After cooling, 8.0 g of brown solid was collected. Recrystallization once from i-PrOH, and once from water gave 1.6 g of the title compound a tan solid, mp 185°–188° (dec.).

Elemental Analysis: Calculated for $C_{18}H_{21}N_2Cl.0.7C_4H_4O_4.0.2H_2O$: C, 64.78; H, 6.32. Found: C, 64.79; H, 6.28.

EXAMPLE 13

3,9a-Dimethyl-4,5,7,8,9,9a-hexahydro-3H-pyrrolo[2,3-]indolizine hydrochloride

Formula (I):

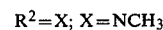

$R^1=CH_3; R^2=H; R^3=H; X=NCH_3$

A solution of 2.04 g (0.01 mole) of 3,9a-dimethyl-4,5,7,8,9,9a-hexahydro-3H-pyrrolo[2,3-g]indolizin-7-one, the compound of Example 11, in 70 ml of ether was added to 0.76 g (0.02 mole) of LAH in 15 ml of ether under argon and allowed to stir overnight. Water (1.5 ml) and 25% sodium hydroxide (0.75 ml) were added and the mixture stirred for two hours. The solids were filtered and washed with ether. Ethereal hydrogen chloride was added to the ether filtrate and the salt filtered. Recrystallization from i-PrOH yielded 1.8 g (80%) of the title compound, mp 279°–281° (dec).

Elemental Analysis: Calculated for $C_{13}H_{18}ClN_2$: C, 63.56; H, 8.45. Found: C, 63.42; H, 8.52.

EXAMPLE 14

3-(2-Aminoethyl)-1-methylpyrrole cyclohexane sulfamate

Formula (III):

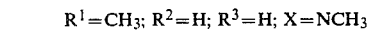

$R^2=X; X=NCH_3$

A solution of 14.7 g of 1-nitro-2-(1-methylpyrrol-3-yl) ethylene prepared by the method shown in U.S. Pat. No. 4,002,643, Example XV in 250 ml of THF was added to a suspension of 11.8 g of LAH in 250 ml of ether at a rate that the mixture refluxed gently. It was heated under reflux for five hours. Water (12 ml), then 12 ml of 10% sodium hydroxide solution, and finally 36 ml of water were added to decompose the excess hydride. The solid was filtered, and washed with THF. The filtrate was evaporated to give 12 g of a yellow oil which was taken up in acetonitrile and 17.4 g (0.11 mole) of cyclohexanesulfamic acid added. The cyclohexanesulfamate salt was collected to give 22 g (74%) of the title compound, mp 153°–155° C.

EXAMPLE 15

1,9a-Dimethyl-4,5,7,8,9,9a-hexahydro-1H-pyrrolo[3,2-g]indolizin-7-one

Formula (VIII):

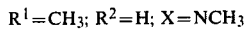

$R^1=CH_3$; $R^2=H$; $X=NCH_3$

A mixture of 6.8 g of 3-(2-aminoethyl)-1-methylpyrrole obtained from the cyclohexanesulfamate salt as prepared in Example 14 and 6.4 g of levulinic acid in 150 ml of benzene was heated to reflux for 2.5 hours. The solution was washed with water, dried over anhydrous magnesium sulfate, and evaporated under reduced pressure to yield 8.0 g of a yellow solid. Recrystallization from ethyl acetate/methylcyclohexane, then from i-PrOH yielded 6.0 g (60%) of the title compound, mp 120°–122° C.

EXAMPLE 16

1,9a-Dimethyl-4,5,7,8,9,9a-hexahydro-1H-pyrrolo[3,2-g]indolizine cyclohexanesulfamate Formula (II):

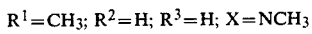

$R^1=CH_3$; $R^2=H$; $R^3=H$; $X=NCH_3$

A solution of 5.1 g of 1,9a-dimethyl-4,5,7,8,9,9a-hexahydro-1H-pyrrolo-[3,2-g]indolizin-7-one, the compound of Example 15, in 50 ml of THF was added dropwise to a suspension of 2.38 g of LAH in 100 ml of ether and stirred overnight at ambient temperature. After the addition of 2.4 ml of water, 2.4 ml of 10% sodium hydroxide, and 7.0 ml of water, the solid was filtered and washed with THF. The filtrate was dried over anhydrous potassium carbonate and evaporated under reduced pressure to give 5.0 g of clear oil. The oil was dissolved in benzene and 4.5 g of cyclohexanesulfamic acid in benzene was added. The resulting salt was filtered and recrystallized from benzene to yield 6.1 g (66%) of the title compound, mp 117°–118° C.

Elemental Analysis: Calculated for $C_{18}H_{31}N_3O_3S$: C, 58.50; H, 8.45. Found: C, 58.44; H, 8.48.

EXAMPLE 17

4,5,7,8,9,9a-alpha-Hexahydro-3-methyl-4-alpha-phenyl-3H-pyrrolo[2,3-g]indolizine and Formula (I):

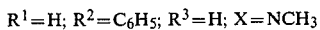

$R^1=H$; $R^2=C_6H_5$; $R^3=H$; $X=NCH_3$ 4,5,7,8,9,9a-beta-Hexahydro-3-methyl-4-alpha-phenyl-3H-pyrrolo[2,3-g]indolizine Formula (I):

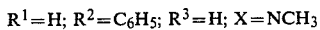

$R^1=H$; $R^2=C_6H_5$; $R^3=H$; $X=NCH_3$

N-Methylpyrrole (54.3 g, 0.67 mole) and ω-nitrostyrene (50.0 g, 0.34 mole) were combined in 115 ml of glyme and 270 ml of dilute $H_2SO_3$ (pH=3). The solution was maintained at 80° C. for eight hours, cooled, diluted with 200 ml of water, and extracted with methylene chloride. The organic layer was washed once with water, once with saturated $NaHCO_3$ solution, and once with saturated NaCl. The solution was dried ($K_2CO_3$) and evaporated in vacuo to a brown solid (77.7 g). The solid was recrystallized from methanol (140 ml) to give a tan crystalline nitroethane product (40.5 g, 52%; mp of a sample recrystallized from methanol, 83°–85° C.). This material (36.3 g, 0.158 mole) in 500 ml of ether was reduced with LAH (17.39 g, 0.474 mole) in 300 ml of ether at room temperature. After 18 hours, 18 ml of water was added dropwise, followed by 18 ml of 15% NaOH, and 54 ml of water. The precipitate was filtered and the ether layer was separated, dried ($K_2CO_3$) and evaporated in vacuo to give an orange solid (22.9 g, 73%) which was 2-[2-(1-methylpyrrol)]phenethylamine. This amine (21.7 g, 0.108 mole) in 150 ml of dry THF was added slowly to succinic anhydride (10.9 g, 0.109 mole) in 100 ml of THF. The solution was evaporated to an oil, which was heated at 175° C. for five hours. The oil was cooled, dissolved in methylene chloride and washed once with 1N HCl, once with 1N NaOH, once with water, once with brine, dried ($MgSO_4$) and evaporated in vacuo to a brown oil (31.0 g), an imide.

The imide (31.0 g) was dissolved in 250 ml of methylene chloride and 250 ml of ethanol cooled to 0° C. and combined with $NaBH_4$ (18.3 g). Methanesulfonic acid (10 drops) was added and the temperature was maintained at 0° C. while every 15 minutes ten drops of a 2N methanesulfonic acid in ethanol was added over the next six hours. Additional acid was added more quickly at 0° C. until adjusted to pH 1 and then the mixture was stirred at room temperature for 16 hours. The reaction was partitioned between methylene chloride and water and the organic solution was washed twice with water, once with brine, dried ($K_2CO_3$) and evaporated in vacuo to give oily lactams (28.4 g). This was combined with 225 ml of DMSO, 10 ml of water and $K_2CO_3$ (75 g) and refluxed under nitrogen for 3.5 hours. The resulting solution was cooled, evaporated in vacuo to half volume and partitioned between chloroform and water. The organic phase was washed twice with water, once with brine, dried ($K_2CO_3$) and evaporated in vacuo to give the lactams in a 70/30 ratio of alpha/beta isomers. This mixture in 40 ml of dry THF was added to 300 ml of 1M $BH_3$.THF solution at 0° C. and refluxed under $N_2$ for one hour. The solution was cooled, 60 ml of water cautiously added followed by 90 ml of 12N HCl and the THF was removed by distillation. The residual aqueous solution was refluxed for 20 minutes, cooled and treated with 10% NaOH to pH 11. The solution was extracted with methylene chloride, which was separated and washed twice with water, once with brine, dried ($K_2CO_3$) and evaporated in vacuo to give 23.9 g of crude amines. The amines were separated by preparative HPLC on silica gel using methylene chloride/methanol (10:1) to give two products: 4,5,7,8,9,9a-alpha-hexahydro-3-methyl-4-alpha-phenyl-3H-pyrrolo[2,3-g]indolizine which was converted to its HBr salt in i-PrOH and recrystallized from i-PrOH to give 6.0 g of white crystals, mp 194°–195° C. Similarly, the 4,5,7,8,9,9a-beta-hexahydro-3-methyl-4-alpha-phenyl-3H-pyrrolo[2,3-g]indolizine isomer (4.6 g) was converted to its HBr salt and recrystallized from i-PrOH to give 1.7 g of white crystals, mp 203°–204° C.

Elemental Analysis: Calculated for (alpha) $C_{17}H_{20}N_2.HBr.1/12C_3H_8O$: C, 61.25; H, 6.46; N, 8.28. Found: C, 61.35; H, 6.41; N, 8.40. Calculated for (beta) $C_{17}H_{20}N_2.HBr.\frac{1}{4}H_2O$: C, 60.45; H, 6.42; N, 8.27. Found: C, 60.46; H, 6.44; N, 8.27.

EXAMPLE 18

4,5,7,8,9,9a-Hexahydro-9a-alpha-methyl-4-alpha-phenylthieno-[2,3-g]indolizine perchlorate (1:1)

Formula (I):

$R^1=CH_3$; $R^2=C_6H_5$; $R^3=H$; $X=S$

Following the procedure of Example 17 but substituting thiophene for N-methylpyrrole, there was produced 2(2-thienyl)phenethylamine as an oil. This oil (7.2 g, 0.03 mole) was treated with 3.0 g of alpha-angelicalactone in 20 ml of methylene chloride. The solution was heated at reflux for ten minutes and the solvent was evaporated. The residue was dissolved in 50 ml of asolute ethanol, treated with 10 ml of ethereal HCl, and heated to remove most of the ether. The mixture was refluxed for four hours then evaporated to dryness. The material was purified by HPLC on silica (ethyl acetate/hexane, 2:1) to give an off-white solid lactam (3.6 g). The lactam (3.5 g, 12.4 mmole) in 40 ml of dry THF was added to 32 ml of 1M borane-THF at 22° C. The reaction was heated at reflux for two hours. After cooling, 10 ml of water was added slowly, followed by 12 ml of concentrated HCl. About 50 ml of THF was removed by distillation and the residue was allowed to cool. It was basified with 3N NaOH and extracted with methylene chloride. The combined extracts were dried (Na$_2$SO$_4$) and concentrated to give a tan, oily amine product (3.5 g). The perchlorate salt was prepared and recrystallized from methanol/ethyl acetate (1:1), affording off-white crystals, mp 216°-219° C. (dec).

Elemental Analysis: Calculated for C$_{17}$H$_{19}$NS.HClO$_4$: C, 55.21; H, 5.45; Cl, 9.58. Found: C, 55.36; H. 5.40; Cl, 8.63.

EXAMPLE 19

4,5,7,8,9,9a-alpha-Hexahydro-4-alpha-phenyl-thieno[2,3-g]indolizine and

Formula (I):

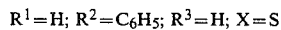

$R^1=H$; $R^2=C_6H_5$; $R^3=H$; $X=S$ 4,5,7,8,9,9a-beta-hexahydro-4-alpha-phenylthieno[2,3-g]indolizine and Formula (I):

$R^1=H$; $R^2=C_6H_5$; $R^3=H$; $X=S$ 4,5,7,8,9,9a-alpha-hexahydro-4-alpha-phenylthieno[3,2-g]indolizine Formula (II):

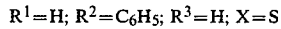

$R^1=H$; $R^2=C_6H_5$; $R^3=H$; $X=S$

2-Amino-1-phenylethanol (100 g, 0.73 mole) was combined with thiophene (150 ml) and cooled in an ice bath as trifluoroacetic acid (175 ml) was added. The reaction was refluxed for 2 hours and then evaporated in vacuo to an oil. The oil was dissolved in methylene chloride and washed once with 5% NaOH, once with water, once with brine, dried (K$_2$CO$_3$) and evaporated in vacuo to an oil (135.8 g). The oil was distilled on a Kugelrohr apparatus (0.8 mm at 140° C.) to give a syrup (90.6 g). This syrup was combined with t-butanol (250 ml) and 30% KOH (810 ml) and refluxed for 18 hours. After cooling, the reaction was extracted with ether and the ethereal solution was washed once with water, once with brine, dried (Na$_2$SO$_4$) and evaporated in vacuo to give a syrup (62.7 g). The syrup was dissolved in ether and HCl gas was bubbled into the solution to give the hydrochloride salt which was recrystallized once from EtOH/Et$_2$O to give a white solid. The salt was converted to its free base by extraction between 5% NaOH and ether and the ethereal solution was dried (Na$_2$SO$_4$) and evaporated in vacuo to give an oil (41.9 g), which was 85% of the 2-thienyl isomer and 15% of the 3-thienyl isomer. This mixture (41.3 g) was combined with succinic anhydride (20.3 g, 0.20 mole) in 150 ml of THF. The solvent was evaporated to an oil which was heated at 150° C. for 40 hours, cooled and dissolved in 50 ml of i-PrOH which rapidly crystallized. After cooling, the white solid imide product was filtered (48.8 g), mp 113°-114° C.

The imide (43.2 g, 0.152 mole) was partially dissolved in 600 ml of EtOH, cooled to 0° C. and NaBH$_4$ (23.0 g, 0.6 mole) was added. The temperature was maintained at −5° to 0° C. while ten drops of methane sulfonic acid was initially added and then over the next three hours 6-8 drops of 2N methanesulfonic acid in ethanol was added every 15 minutes. The temperature was maintained at 0° to 10° C. while the 2N acid was added more quickly over the next 1.5 hours with vigorous stirring to pH 1. The reaction was stirred at room temperature for 16 hours and partitioned between CH$_2$Cl$_2$ and water. The organic layer was washed once with water, once with brine, dried (MgSO$_4$) and evaporated in vacuo to give an oil (43.6 g).

The oil was combined with 400 ml of ethanol and 10 ml of ethereal HCl and refluxed for two hours. The solution was evaporated in vacuo to give white solid lactam products. Separation by preparative HPLC on silica (ethyl acetate/hexane 1:1) gave 4,5,7,8,9,9a-alpha-hexahydro-4-alpha-phenylthieno[2,3-g]indolizin-7-one (19.1 g) and 4,5,7,8,9,9a-alpha-hexahydro-4-alpha-phenylthieno[3,2-g]indolizin-7-one (4.7 g).

4,5,7,8,9,9a-alpha-Hexahydro-4-alpha-phenyl-thieno[2,3-g]-indolizin-7-one (18.9 g) was combined with 150 ml of dimethylsulfoxide, 15 ml of water and 50 g of K$_2$CO$_3$ and refluxed under N$_2$ for two hours. The reaction was cooled and partitioned between water and chloroform. The organic solution was washed three times with water, once with brine, dried (K$_2$CO$_3$) and evaporated in vacuo to give a brown solid (16.9 g). This mixture (2:3) of lactams (14.4 g, 0.054 mole) was dissolved in 50 ml of dry THF and added to 125 ml of 1M BH$_3$.THF in THF at 0° C. The solution was refluxed for 1.5 hours, cooled and water (25 ml) cautiously added, followed by 12N HCl (37.5 ml). The solution was heated to reflux, the THF was removed by distillation and the residual aqueous solution refluxed for another 15 minutes. The solution was cooled, diluted with water (200 ml), adjusted to pH 11 with 10% NaOH and extracted with CH$_2$Cl$_2$. The organic layer was washed once with water, once with brine, dried (K$_2$CO$_3$) and evaporated in vacuo to give the oily amines (11.9 g, 87%). The amines were separated using preparative HPLC on silica (EtOAc/MeOH 19:1) to give 4,5,7,8,9,9a-alpha-hexahydro-4-alpha-phenylthieno[2,3-g]indolizine (5.7 g) and 4,5,7,8,9,9a-beta-hexahydro-4-alpha-phenylthieno[2,3-g]indolizine (5.4 g). The 4,5,7,8,9,9a-alpha-hexahydro-4-alpha-phenylthieno[2,3-g]indolizine amine was converted to its HBr salt and recrystallized from MeOH/i-PrOH to give white crystals (6.0 g) mp 198°-200° C. The 4,5,7,8,9,9a-beta-hexahydro-4-alpha-phenylthieno[2,3-g]indolizine amine was also converted to its HBr salt and recrystallized from MeOH to give white crystals (3.28 g), mp 236°–239° C.

Elemental Analysis: Calculated for $C_{16}H_{17}NS.HBr$: C, 57.15; H, 5.39; N, 4.17. Found (I-alpha): C, 57.16; H, 5.44; N, 4.25. Found (I-beta): C, 57.11; H, 5.44; N, 4.13.

4,5,7,8,9,9a-alpha-Hexahydro-4-alpha-phenyl-thieno[3,2-g]indolizin-7-one (4.0 g) was reduced with 1M $BH_3$.THF (40.0 ml) in a similar manner as above to give 4,5,7,8,9,9a-alpha-hexahydro-4-alpha-phenyl-thieno[3,2-g]indolizine (3.8 g). This was converted to its HBr salt, which was recrystallized from MeOH/i-PrOH to give white crystals (2.62 g), mp 203.5°–205° C.

Elemental Analysis: Calculated for $C_{16}H_{17}NS.HBr$: C, 57.15; H, 5.39; N, 4.17. Found (II-alpha): C, 57.08; H, 5.42; N, 4.20.

EXAMPLE 20

4,5,7,8,9,9a-alpha-Hexahydro-4-alpha-(2-thienyl)-thieno[2,3-g]indolizine and
4,5,7,8,9,9a-beta-hexahydro-4-alpha-(2-thienyl)-thieno[2,3-g]indolizine Formula (I):

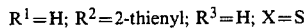

$R^1$=H; $R^2$=2-thienyl; $R^3$=H; X=S

Thiophene (60.0 g, 0.71 mole) and 2-aminoacetalde diethyl acetal (35.4 g, 0.26 mole) were combined in 50 ml of glacial acetic acid. The mixture was cooled to 0° C. and 50 ml of conc. $H_2SO_4$ was added dropwise. The solution was allowed warm to room temperature. The mixture was added to ice water and extracted once with ether. The aqueous solution was basified with 50% NaOH and extracted with methylene chloride. The organic layers were washed once with brine, dried ($K_2CO_3$) and evaporated in vacuo to an oil. The oil was distilled on a Kugelrohr apparatus (1 mm, 150° C.) to give a yellow oily amine (20.4 g). This amine in 90 ml of THF was added slowly to succinic anhydride (9.8 g, 0.098 mole) in 150 ml of THF and the solution was evaporated to an oil which was heated at 140° C. for 12 hours. The oil was dissolved in ethyl acetate, treated with acetyl chloride (20 ml), refluxed for one hour then evaporated in vacuo to an oily amide (23.5 g). This imide in 300 ml of ethanol at 0° C. was combined with NaBH (10.8 g, 0.28 mole) and five drops of methanesulfonic acid were added. The temperature was lowered to −5° C. while every 15 minutes five drops of 2N methanesulfonic acid in ethanol were added over the next four hours. The acid was added more rapidly with vigorous stirring to pH 3 and the mixture stirred at room temperature for 16 hours. The reaction was partitioned between water and methylene chloride and the organic layer was washed once with water, once with brine, dried (MgSO4) and evaporated in vacuo to an oil (23.6 g). The oil was combined with 250 ml of ethanol and 5 ml of ethereal HCl, refluxed for five hours and evaporated to give a mixture of lactams (18.8 g).

The lactams were combined with 150 ml of DMSO, 15 ml of water, 50 g of $K_2CO_3$ and refluxed under $N_2$ for 40 minutes. The solution was cooled and partitioned between water and chloroform. The organic layer was washed twice with water, once with brine, dried (MgSO4) and evaporated in vacuo to give an oil (18.4 g). These lactams were separated by preparative HPLC on silica using ethyl acetate/hexane 1:1 to give the 9a-alpha-4-alpha lactam (8.1 g) and the 9a-beta-4-alpha lactam (6.2 g).

The 9a-beta-4-alpha lactam (5.6 g) in 30 ml of THF was added to 50 ml of 1M $BH_3$ THF and refluxed for 1.5 hours. The cooled solution had 10 ml of water and 15 ml of 12N HCl slowly added and the THF was removed by distillation. The residual aqueous solution was refluxed for ten minutes, cooled, basified with 3N NaOH and extracted with methylene chloride. The organic solution was washed once with water, once with brine, dried ($K_2CO_3$) and evaporated in vacuo to give an oily amine (5.4 g). The amine was converted to its HBr salt in i-PrOH and recrystallized (MeOH/i-PrOH/$Et_2O$) to give white crystals (3.1 g), mp 238°–239° C. of 4,5,7,8,9,9a-beta-hexahydro-4-alpha-(2-thienyl)-thieno[2,3-g]indolizine hydrobromide.

The 9a-alpha-4-alpha lactam (5.8 g) in 25 ml of THF was added to 50 ml of 1M $BH_3$.THF and refluxed for 1.5 hours. Ten ml of water and 15 ml of 12N HCl were added cautiously to the cooled solution and the THF was removed by distillation. The residual aqueous solution was refluxed for ten minutes, cooled and made alkaline with 1N NaOH. The solution was extracted with methylene chloride and the organic solution was washed once with water, once with brine, dried ($K_2CO_3$) and evaporated in vacuo to give a mixture of amines (5.6 g). This mixture was converted to its HBr salt in i-PrOH and recrystallized twice from EtOH and once from MeOH/i-PrOH to give white crystals (2.5 g), mp 187°–189.5° C. of 4,5,7,8,9,9a-alpha-hexahydro-4-alpha-(2-thienyl)thieno[2,3-g]indolizine hydrobromide.

Elemental Analysis: Calculated for $C_{14}H_{15}NS_2.HBr$: C, 49.12; H, 4.71; N, 4.09. Found (alpha): C, 49.47; H, 4.31; N, 4.25. Found (beta): C, 49.16; H, 4.71; N, 4.06.

EXAMPLE 21

4,5,7,8,9,9a-Hexahydro-3-methyl-3H-pyrrolo[2,3-g]indolizin-7-one

Formula (VII):

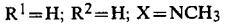

$R^1$=H; $R^2$=H; X=$NCH_3$

A mixture of 110.9 g (1.098 mole) of succinic anhydride and 985 ml of THF was cooled to 10° C. and a solution of 140.53 g (1.098 mole) of 2-(2-aminoethyl)-1-methylpyrrole in 1400 ml of THF was added dropwise over a period of thirty minutes while stirring under an atmosphere of argon, the temperature being maintained at 10 to 15° C. After the addition was complete, stirring was continued an additional one hour and then the solvent removed in vacuo to give a dark-brown, oily residue. The residue was stirred and heated at 175° in an oil bath for three hours under an atmosphere of argon. The residue was distilled on a Kugelrohr apparatus, collecting the product imide at 170° C./0.06 mm, which crystallized to yield an off white solid, mp 116°–121° C. A small sample of the intermediate imide was recrystallized from ethanol to yield a white solid, mp 120°–122° C. A solution of 100 g (0.485 mole) of the above-obtained crude imide was added to 3-1 of 90% aqueous ethanol and the mixture cooled in an ice bath to about 3° C. Sodium borohydride (68.42 g; 1.81 moles) was added and about 25 ml of 2N hydrochloric acid was added dropwise with stirring over a five hour period by means of a metering pump while maintaining a temperature of 0° to 3° C. After the addition was complete (pH=8–9), the reaction was acidified with 1-1 of 2N hydrochloric acid over a period of 1.5 hours while maintaining a temperature of less than 10° C. Stirring (under nitrogen) was continued overnight as the temperature was allowed to gradually warm to ambient, during which time the mixture became a clear, colorless solution. The solvent was partially removed in vacuo using low heat to a final volume of about 800 mls, diluted with 800 mls of water and extracted three times with 300 ml portions of methylene chloride. The combined extracts were washed with 300 ml of water, 300 ml of brine, and dried over anhydrous potassium carbonate. The solvent was removed in vacuo to give 31.07 g of a crude tan solid. The crude solid was recrystallized from about 100 ml of hot EtOAc to give 23.76 g of nearly pure 4,5,7,8,9,9a-hexahydro-3-methyl-3H-pyrrolo[2,3-g]indolizin-7-one, an off-white solid, mp 122°–125° C.

EXAMPLE 22

4,5,7,8,9,9a-Hexahydro-3-methyl-7-phenyl-3H-pyrrolo[2,3-g]indolizine

Formula (I):

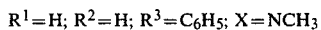

$R^1 = H$; $R^2 = H$; $R^3 = C_6H_5$; $X = NCH_3$

A solution of 18.0 g (0.0946 mole) of 4,5,7,8,9,9a-hexahydro-3-methyl-3H-pyrrolo[2,3-g]indolizin-7-one (the product of Example 21) in 250 ml of dry THF was stirred under an atmosphere of argon in flame-dried glassware at a temperature of 5° to 10° C. while adding 52 ml of 1.82M phenyllithium in ether solution over a period of ten minutes. After the addition was complete, the cooling bath was removed and stirring continued for thirty minutes. The reaction mixture was carefully poured onto 100 g of ice and diluted with about 1–1 of brine. The organics were extracted into three 250 ml portions of ether and the combined extracts washed twice with brine and dried over anhydrous potassium carbonate. The solvent was removed in vacuo to give 23.7 g of a light-brown oily residue.

A slurry of 3.59 g (0.0946 mole) of LAH in 150 ml of anhydrous ether was treated cautiously dropwise with a freshly prepared solution of 12.61 g (0.0946 mole) of anhydrous aluminum chloride in 150 ml of dry ether under an atmosphere of nitrogen in flame-dried glassware. An additional 100 ml of anhydrous ether was added and 23.7 g of the above-isolated oil was carefully added portionwise over a period of about ten minutes. Stirring was continued overnight at room temperature. Water was added cautiously dropwise and the resulting mixture cooled in an ice bath and treated with 3N sodium hydroxide solution to pH>9. An additional 600 ml of water was added and the organics extracted three times with methylene chloride. The combined extracts were washed twice with brine, dried over anhydrous potassium carbonate, and concentrated in vaco to give 19.35 g of a light brown, oily residue, containing an isomeric mixture of 4,5,7,8,9,9a-alpha-hexahydro-3-methyl-7-phenyl-3H-pyrrolo[2,3-g]indolizine and 4,5,7,8,9,9a-beta-hexahydro-3-methyl-7-phenyl-3H-pyrrolo[2,3-g]indolizine. The mixture was separated into its alpha and beta isomers by HPLC, eluting with a solvent mixture of 95:5::toluene:ethyl acetate. The early fractions were combined to give 5.17 g of crude front running isomer and the latter fractions combined to give 3.58 of the slower moving isomer, both as oils. The crude front running isomer obtained in the first fractions was converted to a crude hydrochloride salt by treatment of an isopropanol solution of the oil with a slight excess of anhydrous hydrogen chloride. The crude hydrochloride salt was recrystallized once from MeOH/i-PrOH/Et$_2$O and once from EtOH/Et$_2$O to yield pure first isomer of 4,5,7,8,9,9a-hexahydro-3-methyl-7-phenyl-3H-pyrrolo[2,3-g]indolizine hydrochloride hydrate ethanolate, a white solid, mp 170°–173° C.

In a manner similar to the above, the crude oily slower running isomer obtained from the latter HPLC fractions was converted to its hydrochloride salt. Pure second isomer of 4,5,7,8,9,9a-hexahydro-3-methyl-7-phenyl-3H-pyrrolo[2,3-g]indolizine hydrochloride hydrate 2-propanolate (42:42:7:3) was obtained as a tan solid, mp 181°–183° C., by recrystallization of the crude salt from MeOH/2-PrOH/Et$_2$O.

Elemental Analysis (front running isomer): Calculated for C$_7$H$_{20}$N$_2$.HCl.1/6C$_2$H$_6$O.1/3H$_2$O: C, 68.82; H, 7.55; N, 9.26; H$_2$O, 1.99. Found: C, 68.76; H, 7.53; N, 9.23; H$_2$O, 1.86.

Elemental Analysis (slower running isomer): Calculated for C$_7$H$_{20}$N$_2$.HCl;1/6H$_2$O.1/14C$_3$H$_8$O: C, 69.82; H, 7.46; N, 9.46; HO, 1.01. Found: C, 69.85; H, 7.52; N, 9.43; HO, 0.98.

What is claimed is:

1. A hexahydroindolizine derivative of the following formula (I) or (II):

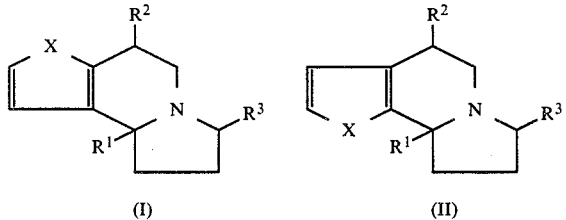

wherein
R$^1$ represents hydrogen, alkyl, or phenyl;
R$^2$ represents hydrogen, phenyl, a thiophene ring, a furan ring, a pyrrole ring, an N-alkylpyrrole ring or phenyl independently substituted with one or more of halogen and alkyl;
R$^3$ represents hydrogen, phenyl or phenyl indepenedently substituted with one or more of halogen, alkyl, alkoxy, or fluoroalkyl;
X represents a sulfur or an oxygen atom or an NR$^4$ group; and,
R$^4$ represents hydrogen, alkyl, phenyl, phenylalkyl, or phenylalkyl wherein the phenyl is independently substituted with one or more of halogen, alkyl, alkoxy, or fluoroalkyl, and the pharmaceutically acceptable acid addition salts thereof with the proviso that when X in formula I is sulfur, R$^2$ is not hydrogen.

2. The hexahydroindolizine of claim 1 wherein
R$^1$ represents hydrogen, loweralkyl of about one to six carbon atoms, or phenyl;
R$^2$ represents hydrogen, phenyl, 2- or 3-thienyl, 2- or 3-furanyl, 2- or 3-pyrrolo, 2- or 3-pyrrolo substituted with loweralkyl of about one to six carbon atoms in the 1-position or phenyl substituted by one, two or three substituents independently selected from halogen or alkyl of about one or six carbon atoms;
R$^3$ represents hydrogen, phenyl or phenyl independently substituted with one or more of halogen, alkyl of about 1 to 6 carbons, alkoxy of about 1 to 6 carbons, or fluoroalkyl of about 1 to 6 carbons;

X represents a sulfur or an oxygen atom or an $NR^4$ group; and, $R^4$ represents hydrogen, alkyl of about 1 to 6 carbons, phenyl, phenylalkyl of about 1 to 6 carbons in the alkyl portion, or phenylalkyl of about 1 to 6 carbons in the alkyl portion wherein the phenyl is independently substituted with one or more of halogen, alkyl of about 1 to 6 carbons, alkoxy of about 1 to 6 carbons, or fluoroalkyl 1 to 6 carbons.

3. The hexahydroindolizine of claim 1 wherein X is $NR^4$.

4. The hexahydroindolizine of claim 1 wherein X is sulfur.

5. The hexahydroindolizine of claim 1 wherein X is oxygen.

6. The hexahydroindolizine of claim 1 wherein $R^1$ is alpha relative to $R^2$.

7. The hexahydroindolizine of claim 1 wherein $R^1$ is beta relative to $R^2$.

8. The hexahydroindolizine of claim 1 wherein said hexahydroindolizine is selected from the group consisting of:
3-(2-chlorobenzyl)-4,5,7,8,9,9a-hexahydro-9a-methyl-3H-pyrrolo[2,3-g]indolizine;
4,5,7,8,9,9a-hexahydro-9a-methyl-3H-pyrrolo[2,3-g]indolizine;
4,5,7,8,9,9a-hexahydro-3-methyl-9a-phenyl-3H-pyrrolo[2,3-g]indolizine;
4,5,7,8,9,9a-hexahydro-9a-methyl-3-phenyl-3H-pyrrolo[2,3-g]indolizine;
7-(4-chlorophenyl)-4,5,7,8,9,9a-hexahydro-3,9a-dimethyl-3H-pyrrolo[2,3-g]indolizine;
3,9a-dimethyl-4,5,7,8,9,9a-hexahydro-3H-pyrrolo[2,3-g]indolizine;
1,9a-dimethyl-4,5,7,8,9,9a-hexahydro-1H-pyrrolo[3,2-g]indolizine;
4,5,7,8,9,9a-alpha-hexahydro-3-methyl-4-alpha-phenyl-3H-pyrrolo[2,3-g]indolizine;
4,5,7,8,9,9a-beta-hexahydro-3-methyl-4-alpha-phenyl-3H-pyrrolo[2,3-g]indolizine;
4,5,7,8,9,9a-hexahydro-9a-alpha-methyl-4-alpha-phenyl-thieno[2,3-g]indolizine;
4,5,7,8,9,9a-alpha-hexahydro-4-alpha-phenyl-thieno[2,3-g]indolizine;
4,5,7,8,9,9a-beta-hexahydro-4-alpha-phenyl-thieno[2,3-g]indolizine;
4,5,7,8,9,9a-alpha-hexahydro-4-alpha-phenyl-thieno[3,2-g]indolizine;
4,5,7,8,9,9a-alpha-hexahydro-4-alpha-(2-thienyl)-thieno[2,3-g]indolizine;
4,5,7,8,9,9a-beta-hexahydro-4-alpha-(2-thienyl)thieno[2,3-g]indolizine; and
4,5,7,8,9,9a-hexahydro-3-methyl-7-phenyl-3H-pyrrolo[2,3-g]indolizine.

9. The hexahydroindolizine of claim 1 wherein said derivative is of the formula (I).

10. The hexahydroindolizine of claim 1 wherein said derivative is of the formula (II).

11. A pharmaceutical composition for inhibiting gastic acid secretion comprising an effective gastric acid secretion inhibiting amount of a hexahydroindolizine of claim 1 in combination with a pharmaceutically acceptable diluent or carrier.

12. A method of inhibiting gastric acid secretion which comprises administering to a mammal in need thereof, the pharmaceutical composition of claim 11.

13. A pharmaceutical composition for alleviating depression comprising an effective anti-depressant amount of a hexahydroindolizine of claim 7 in combination with a pharmaceutically acceptable diluent or carrier.

14. A method of treating depression which comprises administering to a mammal in need thereof, the pharmaceutical composition of claim 13.

15. A propanoic acid derivative of the following formula (V) or (VI):

wherein
$R^1$ represents hydrogen, alkyl, or phenyl;
$R^2$ represents hydrogen, phenyl, a thiophene ring, a furan ring, a pyrrole ring, an N-alkylpyrrole ring or phenyl independently substituted with one or more of halogen and alkyl;
X represents a sulfur or an oxygen atom or an $NR^4$ group; and,
$R^4$ represents hydrogen, alkyl, phenyl, phenylalkyl, or phenylalkyl wherein the phenyl is independently substituted with one or more of halogen, alkyl, alkoxy, or fluoroalkyl.

16. A lactam compound of the following formula (VII) or (VIII):

wherein
$R^1$ represents hydrogen, alkyl, or phenyl;
$R^2$ represents hydrogen, phenyl, a thiophene ring, a furan ring, a pyrrole ring, an N-alkylpyrrole ring or phenyl independently substituted with one or more of halogen and alkyl;
X represents a sulfur or an oxygen atom or an $NR^4$ group; and,
$R^4$ represents hydrogen, alkyl, phenyl, phenylalkyl, or phenylalkyl wherein the phenyl is independently substituted with one or more of halogen, alkyl, alkoxy or fluoroalkyl with the proviso that when X is sulfur and $R^2$ is hydrogen in formula (VII), $R^1$ is not phenyl or methyl.

17. A tetrahydroindolizine compound of the following formula (XIII) or (XIV):

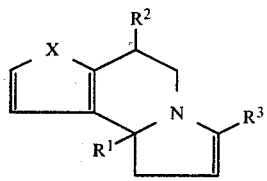
(VIII)

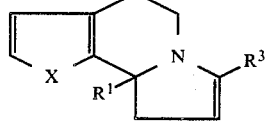
(XIV)

wherein
R¹ represents hydrogen, alkyl, or phenyl;
R² represents hydrogen, phenyl, a thiophene ring, a furan ring, a pyrrole ring, an N-alkylpyrrole ring or phenyl independently substituted with one or more of halogen and alkyl;
R³ represents phenyl or phenyl independently substituted with one or more of halogen, alkyl, alkoxy, or fluoroalkyl;
X represents a sulfur or an oxygen atom or an NR⁴ group; and,
R⁴ represents hydrogen, alkyl, phenyl, phenylaklyl, or phenylalkyl wherein the phenyl is independently substituted with one or more of halogen, alkyl, alkoxy, or fluoroalkyl.

* * * * *